United States Patent
Lee et al.

(10) Patent No.: US 11,718,848 B1
(45) Date of Patent: Aug. 8, 2023

(54) METHODS FOR DEPLETION OF HIGH-COPY SEQUENCES IN MULTIPLEXED WHOLE GENOME SEQUENCING LIBRARIES

(71) Applicant: Color Health, Inc., Burlingame, CA (US)

(72) Inventors: David Lee, San Francisco, CA (US); Justin Lock, San Francisco, CA (US)

(73) Assignee: Color Health, Inc., Burlingame, CA (US)

( * ) Notice: Subject to any disclaimer, the term of this patent is extended or adjusted under 35 U.S.C. 154(b) by 0 days.

(21) Appl. No.: 17/332,610

(22) Filed: May 27, 2021

Related U.S. Application Data

(60) Provisional application No. 63/032,006, filed on May 29, 2020.

(51) Int. Cl.
C12N 15/10 (2006.01)
C12Q 1/6806 (2018.01)

(52) U.S. Cl.
CPC ..... C12N 15/1065 (2013.01); C12N 15/1093 (2013.01); C12Q 1/6806 (2013.01)

(58) Field of Classification Search
None
See application file for complete search history.

(56) References Cited

U.S. PATENT DOCUMENTS

| | | | | |
|---|---|---|---|---|
| 2006/0257902 A1* | 11/2006 | Mendoza | ............. | C12Q 1/6848 435/6.1 |
| 2011/0091939 A1* | 4/2011 | Cui | ............. | C07H 21/04 252/60 |
| 2013/0261027 A1* | 10/2013 | Li | ............. | C12Q 1/6806 506/26 |
| 2015/0119261 A1* | 4/2015 | Richard | ............. | C12Q 1/6806 506/26 |
| 2017/0159040 A1* | 6/2017 | Lock | ............. | C12Q 1/6806 |
| 2018/0291436 A1* | 10/2018 | Wang | ............. | B01L 3/502715 |

FOREIGN PATENT DOCUMENTS

| WO | WO-2020036991 A1 * | 2/2020 | ........... C12Q 1/6832 |
|---|---|---|---|
| WO | WO-2022248237 A1 * | 12/2022 | |

\* cited by examiner

*Primary Examiner* — Aaron A Priest
*Assistant Examiner* — Randi Lynn Beil
(74) *Attorney, Agent, or Firm* — Mughal Gaudry & Franklin PC

(57) ABSTRACT

A depleted sequencing library can be prepared by providing a composition comprising a heterogeneous mixture of linear nucleic acids having a first terminus and a second terminus. A first subset of target nucleic acids and a second subset of non-target nucleic acids can include a first adaptor region at the first terminus and a second adaptor region at the second terminus. A third subset of the target nucleic acids and a fourth subset of the non-target nucleic acids include the second adaptor region at the first terminus and at the second terminus. Removable blocker oligonucleotides can be added to the composition, non-target nucleic acids can be removed from the composition by sequence capture to bait oligonucleotides, and the composition can be treated to reduce a quantity of free blocker oligonucleotides that are not annealed to an adaptor sequence or to a sequence substantially complementary to an adaptor sequence.

17 Claims, 2 Drawing Sheets

Specification includes a Sequence Listing.

METHODS FOR DEPLETION OF HIGH-COPY SEQUENCES IN MULTIPLEXED WHOLE GENOME SEQUENCING LIBRARIES

CROSS-REFERENCE TO RELATED APPLICATION

This application claims priority to U.S. Provisional Application No. 63/032,006, filed May 29, 2020, the disclosure of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Sep. 2, 2021, is named 2021-09-09_098789-002010US-1249857_SL.txt and is 9,924 bytes in size.

BACKGROUND OF THE DISCLOSURE

Whole genome sequencing (WGS) of human DNA is used to discover genomic variants that are associated with human diseases. However, WGS libraries contain sequences that are less informative of monogenic disease, polygenic risk stratification, or non-clinical genetic characteristics. These are typically high-copy sequences, such as repetitive sequence regions and microbial DNAs. Depleting these high-copy sequences from a WGS library would substantially reduce sequencing and computational costs with minimal impact on information content.

Depletion of unwanted sequences in the context of population-scale genome sequencing can be time-consuming and costly if each sample (e.g., nucleic acids from a single patient) needs to be depleted individually. Depletion of multiple samples in a single reaction (i.e., a multiplexed reaction) is substantially more resource efficient and can be achieved by pooling together samples uniquely labeled with indexed adaptors and blocker molecules to prevent adaptor self-hybridization.

SUMMARY OF THE DISCLOSURE

In one aspect, the disclosure provides a method for preparing a depleted sequencing library comprising:

a) providing a composition comprising a heterogeneous mixture of linear nucleic acids that having a first terminus and a second terminus, wherein the mixture comprises a plurality of target nucleic acids and a plurality of non-target nucleic acids, wherein at least some of the plurality of target nucleic acids and at least some of the plurality of non-target nucleic acids comprise an at least partially double-stranded first adaptor region at the first terminus and an at least partially double-stranded second adaptor region at the second terminus and their 5' termini, wherein the first adaptor region comprises a first adaptor sequence and a sequence at least partially complementary to the first adaptor sequence and at least some of the plurality of target nucleic acids and at least some of the plurality of non-target nucleic acids comprise the at least partially double-stranded second adaptor region at the first terminus and the at least partially double-stranded second adaptor region at the second terminus, wherein the second adaptor region comprises a second adaptor sequence and a sequence at least partially complementary to the second adaptor sequence;

b) adding removable blocker oligonucleotides to the composition, wherein the removable blocker oligonucleotides comprise:

(i) first removable blocker oligonucleotides that can anneal to the first adaptor sequence;

(ii) second removable blocker oligonucleotides that can anneal to the second adaptor sequence;

wherein at least one of the removable blocker oligonucleotides selected from the removable blocker oligonucleotides in (i) and (ii) is added in excess over the adaptor sequence to which it hybridizes so that a quantity of said at least one of the removable blocker oligonucleotides is not annealed to an adaptor sequence and is free in solution;

c) removing non-target nucleic acids from the composition by sequence capture to bait oligonucleotides thereby depleting non-target nucleic acids from the composition; and then, d) treating the composition to reduce a quantity of free blocker oligonucleotides that are not annealed to an adaptor sequence or to a sequence substantially complementary to an adaptor sequence, whereby the composition comprises a depleted sequencing library.

In some embodiments of this aspect, also added to the composition are first complementary removable blocker oligonucleotides that can anneal to the sequence substantially complementary to the first adaptor sequence. Further, in some embodiments, second complementary removable blocker oligonucleotides that can anneal to the sequence substantially complementary to the second adaptor sequence can also be added to the composition. In certain embodiments, the first complementary removable blocker oligonucleotides and/or the second complementary removable blocker oligonucleotides are added in excess over the sequence substantially complementary to the adaptor sequence to which it hybridizes so that a quantity of the first and/or second complementary removable blocker oligonucleotides is not annealed to the sequence substantially complementary to the adaptor sequence and is free in solution.

In some embodiments, Step (d) comprises treating the composition to reduce the quantity of the first removable blocker oligonucleotides that are annealed to first adaptor sequences and/or a quantity of the second removable blocker oligonucleotides are annealed to second adaptor sequences.

In some embodiments, the blocker oligonucleotides that are annealed and the blocker oligonucleotides that are not annealed are removed at the same time under the same conditions.

In some embodiments, the method further comprises e) obtaining the plurality of target nucleic acids from the depleted sequencing library; and f) sequencing at least a portion of the plurality of target nucleic acids.

In some embodiments, the removable blocker oligonucleotides are RNA oligonucleotides. In certain embodiments, the removable blocker oligonucleotides are degraded by an enzyme, such as an RNase.

In some embodiments, the removable blocker oligonucleotides are degraded by heat.

In some embodiments, the removable blocker oligonucleotides are degraded by a combination of heat, addition of divalent ions, optionally $Mg^{2+}$, and high pH.

In some embodiments, the removable blocker oligonucleotides are DNA oligonucleotides. In some embodiments, the DNA oligonucleotides comprise uracil. In certain embodiments, the blocker oligonucleotides can be degraded by an uracil-DNA-glycosylase.

In some embodiments, the removable blocker oligonucleotides are from 40 to 80 nucleotides in length.

In some embodiments, the non-target nucleic acids are high copy nucleic acid sequences, transposable elements, tandem repeats, highly transcribed genes, high-copy contaminating DNAs, and/or CRISPR repeats.

In some embodiments, the composition comprises the nucleic acids isolated from multiple samples. In certain embodiments, the nucleic acids from each sample are labeled with a sample-specific barcode sequence.

In some embodiments, the bait oligonucleotides comprise an affinity label (e.g., a biotin group) that enables subsequent capture of the non-target nucleic acids.

DETAILED DESCRIPTION OF THE DISCLOSURE

I. Introduction

Figure 1:
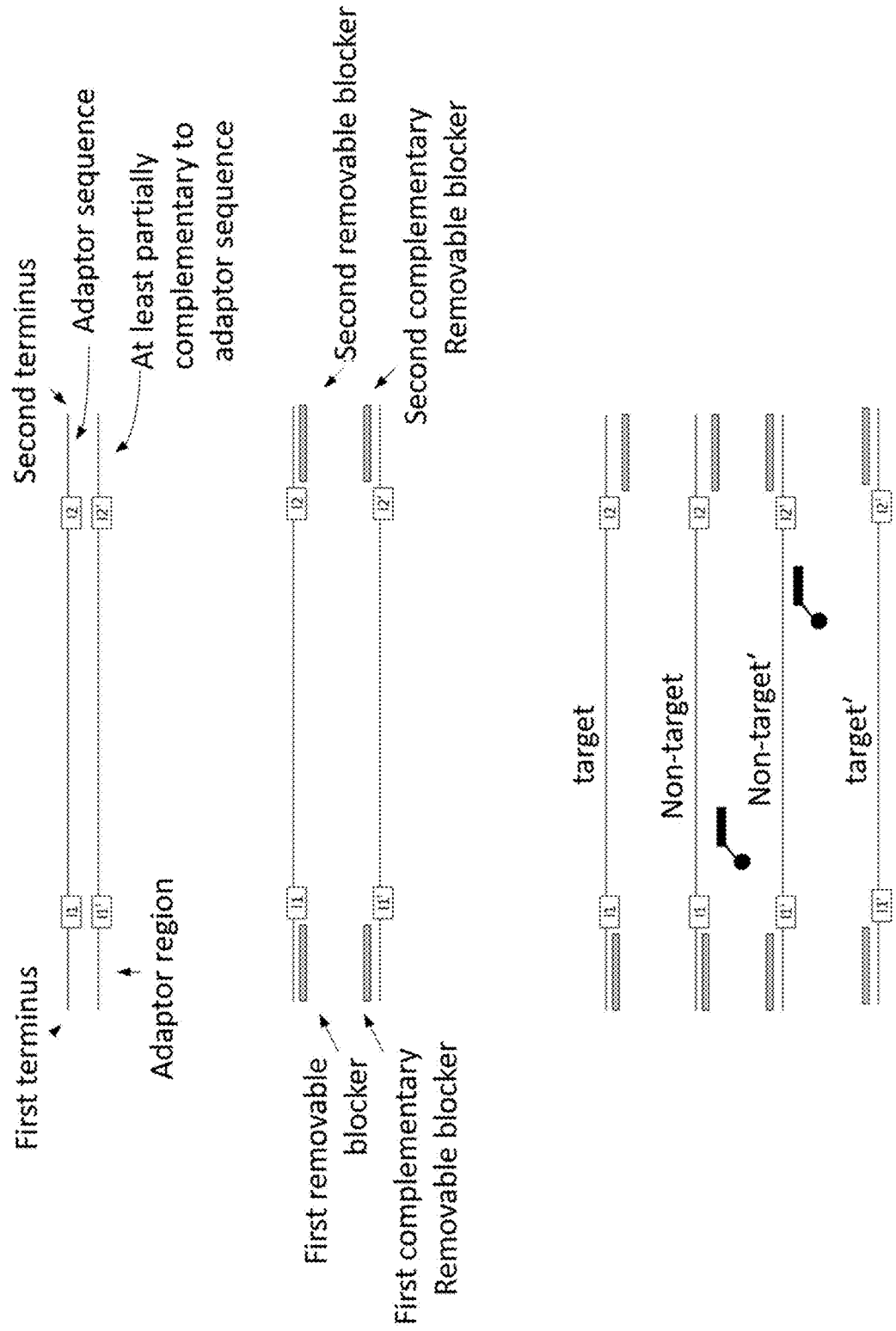
FIG. 1 is provided to illustrate terminology used in the disclosure. I1, I1', I2, and I2' are index sequences. Prime (') indicates a complementary (e.g., substantially complementary) nucleic acid sequence. ⌐ is a bait used in sequence capture of non-target sequences including an oligonucleotide (bar) and an affinity label (dot).

The disclosure provides methods for producing a depleted sequencing library where the proportion of high-copy sequences is reduced. The methods described herein can prevent downstream chemistry inhibition when using the depleted supernatant. A sequencing library, as used herein, contains a heterogeneous mixture of polynucleotides (e.g., representing a whole genome) with adaptors at one or both termini ("adaptored polynucleotides"). Generally the sequencing library is a multiplex library comprising polynucleotides from multiple sources (e.g., multiple human subjects) and are tagged with a barcode or index sequence that identifies the source and optionally provides other information. Typically the polynucleotides and adaptors are double-stranded. In broad terms, a library of adaptored polynucleotides is prepared. Blocking oligonucleotides complementary to and able to hybridize to adaptor sequences are added. The adaptored polynucleotides are denatured to produce single-stranded adaptored polynucleotides and the blocking oligonucleotides are allowed to hybridize to ("block") the adaptor sequences. Subsequently or simultaneously, repeated or high copy number sequences are removed from the mixture by sequence capture. Following sequence capture, the mixture of remaining polynucleotides (e.g., the supernatant), which is now depleted of the high-copy sequences, is treated to remove blocker oligonucleotides. The library comprising the remaining polynucleotides is then sequenced. Multiplexed hybridization reactions may be used in which a supernatant fraction is used for downstream analysis. However, in this approach hybridization reagents such as blocker molecules present in the supernatant can inhibit downstream chemistries. An advantage of the present invention is that such inhibition is avoided.

II. Definitions

As used herein, the term "depleted" in reference to a sequencing library means that the library has been treated to reduce representation of certain sequences such as repeated sequences. "Depleted" does not suggest the complete absence of such sequences from the depleted sequencing library.

As used herein, the term "enrichment" or "enriched" in reference to target nucleic acids refers to increasing the amount of target nucleic acids relative to the amount of non-target nucleic acids of a sample containing both target and non-target nucleic acids. Generally, enrichment involves removing at least a portion of non-target nucleic acids from the nucleic acid sample. Enrichment can be measured by a variety of methods known in the art. In an exemplary embodiment, enrichment can be assessed by subjecting a nucleic acid sample to high-throughput sequencing and counting the number of reads of target and non-target nucleic acid sequences. In some cases, the counts are normalized by removing duplicates and/or correcting for amplification bias. Such normalization can be performed by detecting universal molecule identifiers (e.g., molecular barcodes) as, e.g., described in Fu et al., 2011, Proc Natl Acad Sci USA 108:9026-31. As used herein, unless otherwise indicated, enrichment values refer to the enrichment of a total population of target nucleic acids in a mixture, rather than any one or more individual molecules.

As used herein, the term "target nucleic acid" refers to a nucleic acid molecule (e.g., genomic fragment, cDNA, RNA, mRNA, or a portion thereof) for which enrichment is desired. For example, the target nucleic acids can be molecules that are intended to be a target of a subsequent detection or analysis method, such as high-throughput sequencing.

As used herein, the term "non-target nucleic acid" refers to nucleic acid molecules for which enrichment is not desired and for which depletion is desired. For example, the non-target nucleic acids can be molecules that are not intended to be a target of a subsequent detection or analysis method, such as high-throughput sequencing. Exemplary non-target nucleic acids include, but are not limited to, high-copy sequences, such as genomic fragments containing non-protein coding regions of a genome, repetitive genomic DNA, bacterial sequences, and the like.

As used herein, the term "affinity label" refers to a moiety that has affinity for a capture agent and specifically binds to the capture agent (i.e., the affinity label and capture agent are a "specific binding pair" or SBP). The binding between an affinity label and a capture agent is generally noncovalent, although a covalent (e.g., disulfide) linkage between binding pairs can also be used. A covalent linkage may be reversible or nonreversible. Exemplary binding pairs include, but are not limited to: biotin-avidin, biotin-streptavidin, biotin-neutravidin, biotin-tamavidin, streptavidin binding peptide-streptavidin, antibody-antigen, glutathione-glutathione S-transferase binding pairs, thio (—S—) or thiol (—SH) containing binding member pairs capable of forming an intramolecular disulfide bond, and complementary metal chelating groups and a metal (e.g., metal chelated by the binding pairs nitrilotriacetate (NTA) and a 6×-His tag (SEQ ID NO: 25)). Binding between an affinity label and a capture agent in the specific binding pair results in the formation of a binding complex.

As used herein, the term "bait oligonucleotides" refers to capture oligonucleotides designed to hybridize to non-target nucleic acids in sequence capture methods of the invention.

Bait oligonucleotides can be DNA, RNA, or DNA/RNA chimeras. In some embodiments, the bait oligonucleotide comprises an affinity label that facilitates subsequent isolation by a capture agent. After hybridization of the bait oligonucleotides to non-target nucleic acids to form the non-target nucleic acid:bait oligonucleotide complexes, the complexes can be removed using a capture agent having affinity for the bait. For example, an exemplary affinity label is a biotin moiety, and streptavidin-magnetic beads can be used to bind the biotin moiety of biotinylated baits that are hybridized to the non-target nucleic acids from the nucleic acid sample. For a general description of sequence capture, see, e.g., Mamanova et al., 2010, Target-enrichment strategies for next-generation sequencing, Nature Methods, 7(6), 26-27, incorporated herein by reference.

As used herein, the terms "blocker(s)," "blocker oligonucleotide(s)," "blocker oligo(s)" and the like are used interchangeably and refer to an oligonucleotide that hybridizes to adaptor sequences in a high-throughput sequencing library.

As used herein, the term "complementary" refers to Watson-Crick or Hoogsteen base pairing between nucleotides units of two nucleic acid molecules. Two sequences may be exactly complementary over a defined segment, or substantially complementary. Percent complementarity refers to the percentage of bases of a first nucleic acid molecule that can form Watson-Crick or Hoogsteen base pairs with a second nucleic acid molecule. A nucleic acid molecule having exact complementarity to a second nucleic acid molecule has 100% complementarity to the second nucleic acid molecule over the specified region of contiguous bases.

As used herein, the term "substantially complementary" refers to a nucleic acid molecule having less than 100% complementarity to a second nucleic acid molecule over the specified region of contiguous bases but which has sufficient complementarity to hybridize to the second nucleic acid molecule under conditions of the method disclosed herein (e.g., sequence capture conditions). A nucleic acid molecule segment that is substantially complementary to a second nucleic acid molecule segment has at least one nucleotide that does not form Watson-Crick base pairing with the corresponding nucleotide in the second nucleic acid molecule and may have at least 60% sequence identity, at least 80% sequence identity, or at least 90% sequence identity.

As used herein, the term "at least partially double-stranded" refers to two hybridized polynucleotides in which a portion of a first polynucleotide strand hybridizes to a portion of a second polynucleotide strand to form a double-stranded portion, and at least one of the two polynucleotide strands has an overhang region at the 5' terminus and/or the 3' terminus. In some embodiments, only one of the two polynucleotide strands has an overhang region at its 5' terminus and/or the 3' terminus. In other embodiments, one of the two polynucleotide strands has an overhang at its 5' terminus, while the other polynucleotide strand has an overhang at its 3' terminus.

III. Methods

Described herein are methods for preparing a depleted sequencing library by removing at least some non-target nucleic acid sequences from a mixture of target and non-target nucleic acid sequences in the sequencing library. "Non-target" nucleic acid sequences that are removed may include high-copy sequences such as repetitive sequence regions, microbial DNA, and high-copy contaminating DNAs. High copy sequences may be uninformative of monogenic disease, polygenic risk stratification, non-clinical genetic characteristics, or other information of interest, and depleting these from the sequencing library can substantially reduce sequencing and computational costs with minimal impact on information content. For illustration and not limitation, in some embodiments, non-target nucleic acids that may be removed using the methods described herein include eukaryotic DNA sequences such as transposable elements, retrotransposons (e.g., LINEs, SINEs, and ERV); DNA transposons (e.g., hAT, P element, and PiggyBac)); tandem repeats (e.g., centromeric repeats such as alpha satellite DNA); telomeric repeats; subtelomeric repeats; satellite DNA; minisatellites; microsatellites; highly transcribed genes (e.g., ribosomal RNA genes; transfer RNA genes). In some embodiments non-target nucleic acids originate from prokaryotes such as contaminating bacterial DNA and microbiome DNA. In some embodiments, non-target nucleic acids that can be removed by the methods described herein are high copy number DNA, such as CRISPR repeats.

Adaptors

Libraries prepared for many sequencing platforms comprise a collection of sequences of interest (e.g., a cDNA library or a whole genome library) associated with adaptor sequences, sometimes referred to herein as "adaptored fragments." Methods for preparing a variety of types of sequencing libraries are known; see, e.g., Head et al., 2014, "Library construction for next-generation sequencing: overviews and challenges," Biotechniques 56:61-77, incorporated herein by reference in its entirety. For illustration, some Illumina libraries are constructed by ligating adapters to short (400-1000 bp) linear double-stranded DNA (dsDNA) fragments. Alternatively, adaptors can be introduced into a library by methods other than ligation, such as amplification or tagmentation. Adaptors can be added to a terminus or both termini of a collection of nucleic acids to be sequenced to facilitate high-throughput sequencing. When adaptors are added at both termini of double-stranded fragments, typically different adaptor sequences are introduced to each of the two termini. In some embodiments of the present methods, at least a plurality of target nucleic acids and at least a plurality of non-target nucleic acids comprise a first adaptor sequence at their 5' terminus. In some embodiments, at least a plurality of target nucleic acids and at least a plurality of non-target nucleic acids comprise a second adaptor sequence at their 3' terminus. In other embodiments, at least a plurality of target nucleic acids and at least a plurality of non-target nucleic acids comprise a first adaptor sequence at their 5' terminus and a second adaptor sequence at their 3' terminus.

Generally most or all of the nucleic acid fragments in a mixture prepared for sequencing comprise adaptor sequences in common. For example, all or most of the members of the library may share the same adaptor sequences, usually without regard to whether a member is a target or non-target nucleic acid. In one approach, a multiplex sequencing library contains a plurality of nucleic acids from separate samples (e.g., different sources or individuals), in which the nucleic acids from each sample are tagged with a sample-identifying barcode sequence and can be differentiated based on the barcode. Barcode sequences, also called "index sequences," can be used to enable multiplex sequencing in massively parallel sequencing platforms.

Adaptors may be dsDNA molecules with naturally occurring nucleotides. Alternatively, adaptors may be chimeric nucleic acids, may comprise nucleotides with universal bases, may contain nucleotide analogs or non-naturally occurring backbone structures, be modified for stability or nuclease resistance, and the like. Exemplary modifications include incorporation of phosphorothioate bonds, 2' O methyl nucleotides, 2' fluoro nucleotides, 3' inverted dT nucleotides, 2' deoxyadenosine 5' O (1 thiotriphosphate) nucleotides, and/or 3' phosphorylated nucleotides.

Adaptors can be appended to (e.g., ligated to) any type of target and non-target nucleic acid molecules. In some cases, the adaptors are appended to fragments of the DNA, (e.g., genomic DNA, rDNA, mtDNA, cDNA) or RNA (e.g., mRNA, miRNA, rRNA and the like), in a manner that is sequence independent. In other cases, adaptors are appended in a sequence dependent manner. Adaptors can be appended in a sequence dependent fashion using one or more primers that contain adaptor sequence, or a portion thereof, at the 5' end. In either approach, both target and non-target nucleic acids are associated with the same, common, adaptor sequences. Generally target and non-target nucleic acids are adaptor appended with the same or similar frequency.

Adaptors can be associated with fragments using art-known means. In one example, if the nucleic acids in the library are enzymatically treated to include flush-ended termini, adaptors can be designed to include a first terminus having a flush end and a second terminus having an overhang end. For such adaptors, the second terminus is further designed to include one or more features that preclude ligation to other adaptors (for example, lacking a ligase-competent substrate, such as a 5'-phosphate group, 3'-hydroxyl group, and/or sequence complementarity, among others). In another example, if the nucleic acids in the library are enzymatically treated to include single-nucleotide termini, adaptors can be designed to include a first terminus having a complementary single-nucleotide overhang and a second terminus having a different type of end. Like that described above, the second terminus of the latter adaptors can be preferably designed to include one or more features that preclude ligation to other adaptors. The oligonucleotide composition of adaptors can include conventional nucleobases, wherein the internucleotidyl linkages are conventional phosphodiester moieties. The adaptors can include chemical groups that display Tm-enhanced properties. For illustration and not limitation, the oligonucleotide adaptors can range in length from about 10 to about 100 nucleotides (e.g., 15 nucleotides to about 75 nucleotides; 10 to 100, 40 to 80, 40 to 70, 40 to 60, 40 to 50, 50 to 80, 60 to 80, or 70 to 80 nucleotides in length).

Blocker Oligonucleotides

Following denaturation of double-stranded molecules to form single-stranded polynucleotides (described below), removable blocker oligonucleotides are hybridized to adaptor sequences. Blocker oligonucleotides are associated with adaptors for both target nucleic acid sequences and non-target nucleic acid sequences. The presence of blocker oligonucleotides prevents dimerization, multimerization or concatenation of different nucleic acid fragments (including both target and non-target sequences) that have complementary adaptor sequences (e.g., a single strand of an adaptor on one fragment can anneal to the complementary strand of an adaptor on another fragment). Such multimerization is undesirable because sequence capture and removal of non-target sequences that are part of a multimer with target sequences results in removal of those target sequences.

In one approach, at least two different blocker oligonucleotides are used for each adaptor so that both of the complementary strands of the adaptor sequence are blocked. In this approach, four different blocker oligonucleotides may be used to block two adaptors at the two ends of a fragment, assuming the two adaptors are not identical. In another approach two blocker oligonucleotides may be used to inhibit multimerization by annealing to one strand of a 5' adaptor and one strand of a 3' adaptor. If two blocker oligonucleotides are used they may be designed to block adaptor sequences at opposite termini of the adaptored fragments. In some approaches three blocker oligonucleotides may be used to inhibit multimerization.

In some embodiments, first removable blocker oligonucleotides can be included in or added to the composition, wherein the first removable blocker oligonucleotides can anneal to the first adaptor sequences in the target nucleic acids and non-target nucleic acids. In some embodiments, second removable blocker oligonucleotides can be included in or added to the composition, wherein the second removable blocker oligonucleotides can anneal to the second adaptor sequences in the target nucleic acids and non-target nucleic acids. In other embodiments, both first blocker oligonucleotides and second blocker oligonucleotides can be added to the composition, wherein the first removable blocker oligonucleotides can anneal to the first adaptor sequences at one terminus and the second removable blocker oligonucleotides can anneal to the second adaptor sequences at the other terminus in the target nucleic acids and non-target nucleic acids.

Blocker oligonucleotides can be DNA, RNA, chimeric (comprising both ribonucleotides and deoxyribonucleotides), or are non-naturally occurring analogs (e.g., nucleic acid analogs incorporating phosphorothioate bonds, 2' O methyl nucleotides, 2' fluoro nucleotides, 3' inverted dT nucleotides, 2'-deoxyadenosine-5'-O-(1-Thiotriphosphate) nucleotides, 3' phosphorylated nucleotides, and the like).

The blocker oligonucleotides may be any length, consistent with the intended function. In some embodiments of the method, the removable blocker oligonucleotides are between 10 and 100 nucleotides in length (e.g., 40 to 80, 40 to 70, 40 to 60, 40 to 50, 50 to 80, 60 to 80, or 70 to 80 nucleotides in length).

In some cases, the adaptor sequences can contain one or more regions that are not fully defined, are variable, e.g., a degenerate region, or contain an index sequence that may be unique to the molecule or unique to the source. Such regions can be useful as barcodes for sample tagging, sourcing, molecular counting, tracking, sorting, de-duplication, removal of amplification bias, error correcting, etc. In some cases an index sequence is embedded within an adaptor sequence, or, equivalently, is an intervening sequence between two adaptor sequences, e.g., 5'- . . . [target or non-target sequence]-[adaptor sequence 1]-[index sequence]-[adaptor sequence 2]-3'.

In this case two blocker oligonucleotides may be used to block the two adaptors at each terminus of each strand, along with complementary sequences. In another approach, the blocker oligonucleotide(s) include a "variable binding" region that hybridizes to the index (barcode) sequence between or adjacent to adaptor sequences. In one approach, the variable binding region can contain one or more, or all, universal bases capable of base pairing with any "N" (A, C, G, T), or partially universal bases. Such universal, or partially universal, bases include, but are not limited to, inosine, 5-nitroindole, 2-amino purine, nebularine, and the like. As used herein, a "universal nucleobase" refer to a nucleobase that exhibits the ability to replace any of the four normal nucleobases without significantly destabilizing neighboring base-pair interactions. In another approach, adaptors can include a plurality of nucleotide positions having mixed nucleobase compositions (for example, a mixture of two or more canonical nucleobases at a particular position(s), including "universal" nucleobase compositions) that represent the barcode sequence tags. When such variable binding regions are present in adaptor regions, they may occupy a plurality of substantially contiguous nucleotide positions ranging in length, preferably from about 5 to about 25 nucleotides.

In some embodiments the blocker oligonucleotides are added in excess compared to the adaptor sequences to which the blockers bind. In some embodiments of the method, the molar amount of first removable blocker oligonucleotides is greater than the molar amount of the first adaptor sequence in the composition, and/or the molar amount of second removable blocker oligonucleotides is greater than the molar amount of the second adaptor sequence in the composition, such that a first amount of the first removable blocker oligonucleotides are not annealed to first adaptor sequences and/or a first amount of the second removable blocker oligonucleotides are not annealed to second adaptor sequences.

Capture and Depletion

High-copy sequences (non-target nucleic acids) are removed or partially removed from the mixture in a process referred to as "depletion." In one approach sequence capture using bait oligonucleotides designed to hybridize to the non-target nucleic acids is used. Sequence capture using bait nucleic acid is well known. See, for example, Albert et al., 2007, "Direct selection of human genomic loci by microarray hybridization," Nature Methods, 4:903-905; Glenn, T. C., & Faircloth, B. C., 2016, "Capturing Darwin's dream," Molecular Ecology Resources 16:1051-1058; Grover et al., 2012, "Targeted sequence capture as a powerful tool for evolutionary analysis," American Journal of Botany 99:312-319; Jones, M. R., & Good, J. M., 2016, "Targeted capture in evolutionary and ecological genomics," Molecular Ecology, 25:185-202; Lemmon et al., 2012, "Anchored hybrid enrichment for massively high-throughput phylogenomics," Systematic Biology, 61:727-744; Lemmon & Lemmon, 2013, "High-throughput genomic data in systematics and phylogenetics," Annual Review of Ecology, Evolution, and Systematics, 44:99-121; and Mamanova et al., 2010, "Target-enrichment strategies for next-generation sequencing," Nature Methods, 7:26-27, each of which is incorporated herein by reference. The person skilled in the art will recognize that many different terms are used to refer to "sequence capture," including "hybrid capture," "hybridization capture," "solution hybridization capture," "solution-phase hybrid selection," and others.

When hybridization is complete to form the non-target nucleic acid:bait hybrids, capture is performed with a capture agent having a specific affinity for the affinity label in the bait. For example, streptavidin-magnetic beads can be used as the capture agent to bind the biotin moiety of biotinylated-baits that are hybridized to the desired non-nucleic acids from the pool of target and non-target nucleic acids. The retained material (e.g., supernatant) which contains the target nucleic acids is then collected.

The nucleic acid portion of bait oligonucleotides can contain or consist of DNA, RNA, or a combination thereof. In some cases, the bait oligonucleotides contain one or more nucleotide modifications. For example, the bait oligonucleotides can contain a nucleotide modification that increases the melting temperature of a [bait oligonucleotide]:[non-target nucleic acid molecule] complex. Examples, of such modifications include, but are not limited to, locked nucleic acid groups, bicyclic nucleic acid groups, C5-modified pyrimidine groups, peptide nucleic acid groups, and combinations thereof. In a non-limiting aspect, the bait oligonucleotides are capable of hybridizing or binding to non-target nucleic acids that are at least 70%, at least 80%, at least 85%, at least 90%, at least 95%, at least 96%, at least 97%, at least 98%, at least 98%, at least 99%, or 100% identical to a complementary sequence of a bait oligonucleotide. In an exemplary embodiment, the bait oligonucleotides are 120 bp DNA molecules that are covalently linked to a biotin moiety at the 5' end.

The concentration of bait oligonucleotides can be at least about 0.2 pmol/µL, at least about 0.3 pmol/µL, at least about 0.4 pmol/µL, at least about 0.5 pmol/µL, at least about 0.6 pmol/µL, at least about 0.7 pmol/µL, at least about 0.8 pmol/µL, at least about 0.9 pmol/µL, at least about 1 pmol/µL, or more. In some cases, the concentration of bait oligonucleotides is not less than about 0.2 pmol/µL and not more than about 100 pmol/µL (e.g., between 1 and 100 pmol/µL, between 10 and 100 pmol/µL, between 20 and 100 pmol/µL, between 30 and 100 pmol/µL, between 40 and 100 pmol/µL, between 50 and 100 pmol/µL, between 60 and 100 pmol/µL, between 70 and 100 pmol/µL, between 80 and 100 pmol/µL, between 90 and 100 pmol/µL, between 1 and 90 pmol/µL, between 1 and 80 pmol/µL, between 1 and 70 pmol/µL, between 1 and 60 pmol/µL, between 1 and 50 pmol/µL, between 1 and 40 pmol/µL, between 1 and 30 pmol/µL, between 1 and 20 pmol/µL, or between 1 and 10 pmol/µL). In some cases, the concentration of bait oligonucleotides in the aqueous reaction mixture can be at least 0.75 pmol/µL. For example, the concentration of bait oligonucleotides in the aqueous reaction mixture can be from about 0.5 pmol/µL to about 2 pmol/µL, from about 0.6 pmol/µL to about 2 pmol/µL, from about 0.7 pmol/µL to about 2 pmol/µL, from about 0.75 pmol/µL to about 2 pmol/µL, from about 1 pmol/µL to about 2 pmol/µL, or about 1.5 pmol/µL.

Removing Blocker Oligonucleotides

In one aspect the method involves treating the composition to reduce a quantity of blocker oligonucleotides. It will be understood that blocker oligonucleotides will have at least one structural feature that allows them to be degraded and/or physically removed from a mixture prior to sequencing. Blocker oligonucleotides are added to multiplexed reactions to prevent the formation of concatemers among sequences, which would lead to hybridization of the target sequences to be sequenced and the high-copy sequences to be removed. As described herein, the reaction can then be specifically separated into a capture fraction that contains the non-target nucleic acids and a supernatant fraction that contains the target nucleic acids. Since the supernatant fraction is used for sequencing, the high concentration of free blocker oligonucleotides present in the supernatant fraction can inhibit downstream chemistries such as amplification high-throughput sequencing of the target nucleic acids. Additionally, the blocker oligonucleotides that hybridize to the adaptor oligonucleotides and prevent the hybridization and concatemer formation between target nucleic acids and non-target nucleic acids can be removed from the supernatant fraction prior to downstream procedures. The blocker oligonucleotides can be designed to facilitate removal.

In some embodiments, after the non-target nucleic acids are removed, the composition can be treated to reduce a quantity of the first removable blocker oligonucleotides that are not annealed to first adaptor sequences and/or a quantity of the second removable blocker oligonucleotides are not annealed to second adaptor sequences whereby the composition comprises a depleted sequencing library. In some embodiments, after the non-target nucleic acids are removed, the composition can be treated to reduce a quantity of the first removable blocker oligonucleotides that are annealed to first adaptor sequences and/or a quantity of the second removable blocker oligonucleotides are annealed to second adaptor sequences whereby the composition comprises a depleted sequencing library.

Exemplary methods and techniques for removing the blocker oligonucleotides are provided below.

Methods for Removing (e.g., Degrading) RNA Blocker Oligonucleotides

A blocker oligonucleotide can be an RNA blocker oligonucleotide. Several methods can be used to remove RNA blocker oligonucleotides, such as degradation using enzymes, heat, divalent ions, and/or pH.

Treatment with RNAse

As described herein, after the reaction is separated into a capture fraction that contains the non-target nucleic acids and a supernatant fraction that contains the target nucleic acids, the supernatant fraction can be isolated and a ribonuclease (RNase) can be added to the fraction. RNase catalyzes the degradation of RNA into smaller components including monomers. Different types of RNases have different specificities towards RNA molecules. For example, RNases may be can be classified as endoribonucleases or exoribonucleases. Examples of RNases useful in the present method include, but are not limited to, RNase A, RNase H, RNase III, RNase L, RNase P, RNase PhyM, RNase T1, RNase T2, RNase U2, and RNase V.

RNase A is specific for single-stranded RNAs. In some embodiments, a RNase A can be used to cleave the blocker oligonucleotides present in the supernatant fraction containing the target nucleic acids to be sequenced. RNase H is a non-specific endonuclease that cleaves the RNA in a DNA/RNA duplex to produce single-stranded DNA. RNase H can be used to cleave the blocker oligonucleotides that are hybridized to the target nucleic acids. RNase H catalyzes the cleavage of RNA via a hydrolytic mechanism, aided by an enzyme-bound divalent metal ion. RNase PhyM is specific for single-stranded RNAs and cleaves 3'-end of unpaired A and U residues. RNase T1 is a guanylic-acid specific endonuclease that cleaves 3'-end of unpaired G residues in sequence specific for single-stranded RNAs. RNase T2 is an endonuclease that exhibits base preference in the following order: A>G>C, U. RNase U2 is an endonuclease that exhibits base preference for single-stranded RNAs and cleaves 3'-end of unpaired A residues. RNase V is specific for polyadenine and polyuridine RNA.

As described above, depending on the type of RNase to be used, a skilled artisan can design the blocker oligonucleotides such that they can be degraded by the RNase of choice. A RNase can be added to the supernatant fraction containing the nucleic acids to be sequenced and the reaction can be incubated for a period of time at a specific temperature under a condition that is optimal for the RNase to be active. For example, a RNase A treatment often involves incubating the reaction for about 15 to 30 minutes at about 37° C.

Degradation of RNA at Elevated Temperature

Another method to remove RNA blocker oligonucleotides by incubating the supernatant fraction at an elevated temperate for a period of time. RNA is made up of ribose units, which have a highly reactive hydroxyl group on the C2 carbon. This nature makes RNA more chemically labile than DNA and also more prone to heat degradation. At an elevated temperature, heat can increase the rate of hydrolysis of the phosphodiester bond in RNA. For example, to remove RNA blocker oligonucleotides using heat, the supernatant fraction can be incubated at at least 70° C. (e.g., about 75° C., about 80° C., about 85° C., about 90° C., or about 95° C.) for at least 1 minute, such as 2 to 30 minutes (e.g., 2, 5, 10, 15, 20, 25, or 30 minutes). In particular, the supernatant fraction can be incubated at about 95° C. for about 10 minutes.

Degradation of RNA in the Presence of Divalent Ions

The presence of divalent ions can also destabilize and denature RNA molecules due to the chelation effect between the divalent ion and the RNA oligonucleotide. Examples of divalent ions that can be added to the supernatant fraction include, e.g., $Mg^{2+}$, $Ca^{2+}$, $Be^{2+}$, $Sr^{2+}$, $Ba^{2+}$, and $Ra^{2+}$. In particular, $Mg^{2+}$ is effective when added to the supernatant fraction. A skilled artisan can determine the concentration of the divalent ion, the temperature, and duration of time at which the supernatant fraction can be incubated with the divalent ion in order to denature the RNA blocker oligonucleotides.

Degradation of RNA at High pH

In some embodiments, the supernatant fraction containing the target nucleic acids to be sequenced can be incubated at a basic condition, e.g., at a pH greater than 7 (e.g., at a pH from 7.5 to 9.5 (e.g., from 7.5 to 9, from 7.5 to 8.5, from 7.5 to 8, from 8 to 9.5, from 8.5 to 9.5, or from 9 to 9.5, or about 7.5, 8, 8.5, 9, 9.5, 10, 10.5, 11, 11.5, 12, 12.5, 13, 13.5, or 14). The pH of the supernatant fraction can be adjusted as appropriate.

Combinations

In certain embodiments, two or more conditions described above can be used in combination to degrade RNA blocker oligonucleotides in the supernatant fraction. For example, the supernatant fraction can be added $Mg^{2+}$ ions and incubated at an elevated temperate. In another example, the supernatant fraction can be adjusted to a pH of between 7.5 and 9.5 and incubated at an elevated temperature (e.g., at least 70° C.).

Methods for Removing RNA or DNA Blocker Oligonucleotides with Attached Moieties

A blocker oligonucleotide can be designed to include an attached moiety that can be used to selectively capture and remove the blocker oligonucleotides. In one example, a blocker oligonucleotide can contain an affinity label, such as a biotin group, which would allow the selective capture of blocker oligonucleotides from the supernatant fraction via streptavidin-coated magnetic beads. In this example, the affinity label used on the blocker oligonucleotide must be different from the affinity label used in the bait oligonucleotide to still enable the selective removal of the non-target nucleic acids. For example, the affinity label on the bait oligonucleotides can be a biotin group to selectively remove non-target nucleic acids via biotin-streptavidin interaction, and the affinity label on the blocker oligonucleotides can be a 6×-His tag (SEQ ID NO: 25) to selectively remove the blocker oligonucleotides via Ni-6×-His interaction.

Another attached moiety that can be conjugated to blocker oligonucleotides is a digoxigenin (DIG) moiety. Digoxigenin (DIG) is a steroid found exclusively in the flowers and leaves of the plants *Digitalis purpurea, Digitalis orientalis*, and *Digitalis lanata*. DIG-binding proteins (see, e.g., Tinberg et al., *Nature.* 501(7466):212-216, 2013) and anti-DIG antibodies (e.g., commercially available at Abcam) are available to be used as the capture agent to selectively remove DIG-conjugated blocker oligonucleotides. For example, the supernatant fraction containing blocker oligonucleotides conjugated with DIG moieties can be incubated with anti-DIG antibody-coated magnetic beads to remove the blocker antibodies.

In another example, chemical functional groups can be used as attached moieties on blocker oligonucleotides. The chemical functional groups can react with their complementary functional groups to selectively remove blocker oligonucleotides. Complementary chemical functional groups on two components can react with each other to form a covalent bond. Examples of complementary chemical functional groups include, but are not limited to, e.g., amine and activated carboxylic acid, thiol and maleimide, activated sulfonic acid and amine, isocyanate and amine, azide and alkyne, and alkene and tetrazine. For example, a blocker oligonucleotide can contain azide chemical functional groups as the attached moiety, which can react with the alkyne (e.g., a terminal alkyne or an internal alkyne) functional groups on alkyne-coated magnetic beads to form 1,2,3-triazole groups to remove the blocker oligonucleotides.

Methods to Remove Blocker Oligonucleotides Containing Uracil Bases

In some embodiments, DNA blocker oligonucleotides are designed to contain deoxyribouracil nucleotides. An uracil-DNA glycosylase is an enzyme that can cleave the N-glycosidic linkage between the uracil nucleobase and its 5-carbon sugar. For example, once the non-target nucleic acids are removed, the supernatant containing the target nucleic acids and free blocker oligonucleotides can be incubated with uracil-DNA glycosylases, for example, at about 37° C. for a duration between 10 minutes to 30 minutes. Once the uracil nucleobases are cleaved from the blocker oligonucleotides by the uracil-DNA glycosylase, the remaining blocker oligonucleotides are labile to acid or base hydrolysis. Further, the uracil-DNA glycosylase can be inactivated by heat denaturation before subsequent sequencing of the target nucleic acids. DNA blocker oligonucleotides may contain at least 1, at least 2, at least 3, at least 4, at least 5, at least 6 or more uracil nucleotides. At least ten percent, at least 20%, at least 30%, at least 50%, at least 75%, at least 90% or 100% of the nucleotides in a blocker oligonucleotide may be uracil. DNA blocker oligonucleotides may contain at least 1, at least 2, at least 3, at least 4, at least 5, at least 6 or more uracil nucleotides.

Methods to Remove Unmodified DNA Blocker Oligonucleotides

In some embodiments, the blocker oligonucleotide can be a DNA blocker oligonucleotide that contains unmodified DNA nucleotides. Size selection can be used to separate DNA blocker oligonucleotides if the length of the DNA blocker oligonucleotides is substantially different from the target nucleic acids. For example, if the target nucleic acid is about 500 bp and the blocker oligonucleotide is 80 bp, then the blocker oligonucleotide can be separated from the target nucleic acid by techniques such as DNA binding beads, agarose gel electrophoresis, and liquid chromatography. Further, photocleavable spacers can be placed within the DNA blocker oligonucleotides, such that the DNA blocker oligonucleotides can be photo-fragmented into smaller sizes prior to size selection and separation.

Methods to Remove Blocker Oligonucleotides Using Antibody-Oligo Conjugates

In some embodiments, oligonucleotide-conjugated antibodies can be used to remove blocker oligonucleotides. An oligonucleotide that is complementary to the blocker oligonucleotide or a portion of the blocker oligonucleotide can be conjugated to an antibody. Oligonucleotide-conjugated antibodies can then be used to selectively pull out and separate blocker oligonucleotides from the target nucleic acids. Techniques to conjugate oligonucleotides to antibodies are available in the art, see, e.g., Dovgan et al., *Bioconjugate Chemistry*. 30:(10):2483-2501, 2019; and Winkler, *Therapeutic Delivery. Future Science Ltd.* 4(7): 791-809, 2013. For example, in some embodiments, Thunder-Link conjugation process (Innova Biosciences) can be used to generate oligonucleotide-conjugated antibodies, in which the oligonucleotide is complementary to the blocker oligonucleotide or a portion thereof. In Thunder-Link conjugation, the oligonucleotide is modified with a terminal amine at the 5' or 3' terminus of the oligonucleotide.

IV. Sequencing Methods

Following degradation or diminution of free and annealed blocker oligonucleotides in the supernatant fraction, target polynucleotides may be collected and sequenced using routine methods. In some methods the polynucleotides from the supernatant are amplified (e.g., for cluster generation) amplification (e.g. for cluster generation). Removal of the oligonucleotide blockers allows correct and efficient amplification. In contrast, if oligonucleotide blockers are not removed they may interfere with sequencing by a variety of mechanisms, including blocking primer annealing to primer binding sites in the adaptors.

The methods described herein are compatible with a variety of NGS platforms including platforms compatible with Illumina sequencing technology and platforms developed by Life Technologies, Roche, and Pacific Biosciences.

The methods described herein can be also used for applications that require sequencing at different depths or coverages. For example, a low sequencing coverage, such as 1× average genome coverage, can be used for applications such as ancestry determination and polygenic risk scoring. A medium sequencing coverage, such as 5-15× average genome coverage, can be used for applications such as SNP determination and indel calling and discovery. A high sequencing coverage, such as 30× average genome coverage, can be used for applications such as complete germline variant calling, including large structural variants. Finally, an ultra-high sequencing coverage, such as up to 100-200× average genome coverage, can be used for applications such as calling of low allele fraction variants, e.g., such as somatic variants in cancer.

V. Workflow

Generally double-stranded adaptored polynucleotides are denatured prior to adaptor blocking and sequence capture steps. Double-stranded DNA is typically denatured using heat, basic pH, or high salt, or a combination of these. Preferably a denaturation method is selected to avoid introduction of elements into the supernatant that will interfere with downstream sequencing.

In one approach, double-stranded adaptored DNA fragments, bait oligonucleotides, and blocker oligonucleotides are combined, the DNA is denatured and the blocker oligonucleotides and bait oligonucleotides are allowed to anneal to the corresponding complementary sequences on the target and non-target polynucleotides. Alternatively, double-stranded adaptored DNA fragments can be denatured and bait oligonucleotides and blocker oligonucleotides added in either order or together.

Using the present method, following removal of non-target sequences by sequence capture and reduction of blocker oligonucleotides, target polynucleotides can be amplified and sequenced without further purification (e.g., without physical removal of oligonucleotide blockers from the supernatant).

VI. Sequencing Applications

The methods described herein can be used for performing whole genome genetic analysis, for example, genetic analysis on cancer cells from different a cancer patients. The methods described herein can also be used to perform certain prenatal diagnosis, such as genetic analysis of fetal and maternal nucleic acids. The methods describe herein can also be used to perform genetic analysis of germline variants (e.g., germline variants described in U.S. Pat. No. 10,266,889, in particular, Table 1 in Example F). Examples of general categories of cancer include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells), blastic tumors and the like. One of skill in the art will understand that this list is exemplary only and is not exhaustive, as one of skill in the art will readily be able to identify additional cancers based on the disclosure herein.

Examples of specific neoplasms intended to be encompassed by the present invention include, but are not limited to, acute lymphoblastic leukemia; myeloid leukemia, acute myeloid leukemia, childhood; adrenocortical carcinoma; AIDS-, related cancers; AIDS-related lymphoma; anal cancer; appendix cancer; astrocytoma (e.g., cerebellar, cerebral); atypical teratoid/rhabdoid tumor; basal cell carcinoma; bile duct cancer, extrahepatic; bladder cancer; bone cancer, osteosarcoma and malignant fibrous histiocytoma; brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors); breast cancer; bronchial tumors; Burkitt lymphoma; carcinoid tumor (e.g., gastrointestinal); carcinoma of unknown primary; central nervous system (e.g., atypical teratoid/rhabdoid tumor, embryonal tumors (e.g., lymphoma, primary); cerebellar astrocytoma; cerebral astrocytoma/malignant glioma; cervical cancer; chordoma; chronic lymphocytic leukemia; chronic myelogenous leukemia; chronic myeloproliferative disorders; colon cancer; colorectal cancer; craniopharyngioma; cutaneous T-cell lymphoma; embryonal tumors, central nervous system; endometrial cancer; ependymoblastoma; ependymoma; esophageal cancer; Ewing family of tumors; extracranial germ cell tumor; extragonadal germ cell tumor; extrahepatic bile duct cancer; eye cancer (e.g., intraocular melanoma, retinoblastoma); gallbladder cancer; gastric cancer; gastrointestinal tumor (e.g., carcinoid tumor, stromal tumor (gist), stromal cell tumor); germ cell tumor (e.g., extracranial, extragonadal, ovarian); gestational trophoblastic tumor; glioma (e.g., brain stem, cerebral astrocytoma); hairy cell leukemia; head and neck cancer; hepatocellular cancer; Hodgkin lymphoma; hypopharyngeal cancer; hypothalamic and visual pathway glioma; intraocular melanoma; islet cell tumors; Kaposi sarcoma; kidney cancer; large cell tumors; laryngeal cancer (e.g., acute lymphoblastic, acute myeloid); leukemia (e.g., acute myeloid, chronic lymphocytic, chronic myelogenous, hairy cell); lip and/or oral cavity cancer; liver cancer; lung cancer (e.g., non-small cell, small cell); lymphoma (e.g., AIDS-related, Burkitt, cutaneous Tcell, Hodgkin, non-Hodgkin, primary central nervous system); macroglobulinemia, Waldenstrom; malignant fibrous histiocytoma of bone and/or osteosarcoma; medulloblastoma; medulloepithelioma; melanoma; merkel cell carcinoma; mesothelioma; metastatic squamous neck cancer; mouth cancer; multiple endocrine neoplasia syndrome; multiple myeloma/plasma cell neoplasm; mycosis fungoides; myelodysplastic syndromes; myelodysplastic/myeloproliferative diseases; myelogenous leukemia (e.g., chronic, acute, multiple); myeloproliferative disorders, chronic; nasal cavity and/or paranasal sinus cancer; nasopharyngeal cancer; neuroblastoma; non-Hodgkin lymphoma; non-small cell lung cancer; oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor); pancreatic cancer (e.g., islet cell tumors); papillomatosis; paranasal sinus and/or nasal cavity cancer; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma cell neoplasm/multiple myeloma; pleuropulmonary blastoma; primary central nervous system lymphoma; prostate cancer; rectal cancer; renal cell cancer; renal, pelvis and/or ureter, transitional cell cancer; respiratory tract carcinoma involving the nut gene on chromosome 15; retinoblastoma; rhabdomyosarcoma; salivary gland cancer; sarcoma (e.g., Ewing family of tumors, Kaposi, soft tissue, uterine); Sézary syndrome; skin cancer (e.g., non-melanoma, melanoma, merkel cell); small cell lung cancer; small intestine cancer; soft tissue sarcoma; squamous cell carcinoma; squamous neck cancer with occult primary, metastatic; stomach cancer; supratentorial primitive neuroectodermal tumors; T-cell lymphoma, cutaneous; testicular cancer; throat cancer; thymoma and/or thymic carcinoma; thyroid cancer; transitional cell cancer of the renal, pelvis and/or ureter; trophoblastic tumor; unknown primary site carcinoma; urethral cancer; uterine cancer, endometrial; uterine sarcoma; vaginal cancer; visual pathway and/or hypothalamic glioma; vulvar cancer; Waldenstrom macroglobulinemia; Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

VII. Examples

The present disclosure will be described in greater detail by way of specific examples. The following examples are offered for illustrative purposes only, and are not intended to limit the disclosure in any manner. Those of skill in the art will readily recognize a variety of noncritical parameters which can be changed or modified to yield essentially the same results.

A. Example 1. Multiplex Library Preparation

For each sample, 200 ng of double-stranded DNA in 35 µl of 10 mM Tris-HCl (pH 8.0) was prepared. Library preparation was performed using the Kapa HyperPlus Kit (Roche #07962428001) as follows. A 15 µl enzymatic fragmentation mastermix was prepared for each sample with 5 µl of KAPA Frag Buffer (10×) and 10 µl of KAPA Frag Enzyme, then aliquoted into each 35° C. DNA sample. Reaction mixes were gently vortexed and centrifuged then placed in a thermocycler pre-cooled to 4° C. The reactions were incubated at 37° C. for 15 minutes then set on ice. An end repair and A-tailing master mix was prepared for each sample with 7 µl of End Repair & A-tailing Buffer and 3 µl of HyperPlus ERAT Enzyme Mix and aliquoted into each 50 µl fragmentation mix. Reaction mixes were gently vortexed and centrifuged then incubated in a thermocycler at 65° C. with a 85° C. heated lid for 30 minutes, then cooled to 4° C. A 50 µl ligation master mix was prepared for each sample with 5 µl of nuclease-free water, 30 µl of Ligation Buffer, 10 µl of DNA ligase, and 2.5 µl each of 15 µM adapter unique dual indexed adapters from the KAPA Unique Dual-Indexed Adapter kit (Roche 8861919702) and aliquoted into each 60 µl reaction. Indexes were arranged such that each sample has a unique index pair. The reactions were pipette mixed then centrifuged and incubated at 20° C. for 15 minutes. Reactions were cleaned up using KAPA pure beads (Roche #07983271001) as follows. Purification beads were resuspended and warmed to room temperature, then 88 µl of beads pipette mixed with the 110 µl reaction. After incubation for 3 minutes, the mixture was applied to a magnetic rack and the supernatant discarded. The beads were washed twice with freshly prepared 80% ethanol while still on the magnetic rack, then eluted in 20 µl of 10 mM Tris-HCl (pH 8.0) to produce the purified libraries.

B. Example 2. Synthesis of Biotinylated Probes for Repetitive Sequence Depletion To create biotinylated probes for repeat depletion, biotin labeling of human $C_0T$-1 DNA (Thermo Fisher, #15279011) was performed using the Enzo translation DNA labeling system 2.0 (Enzo Life Sciences, #ENZ-42910) as follows. A nick translation mix consisting of 5 µl nick translation buffer, 5 µl of dNTP mix (dATP, dGTP, dCTP), 1.7 µl of dTTP, 3.3 µl of 0.3 mM Bio-16-dUTP (Enzo Life Sciences, #ENZ-42811), 5 µl of NT enzyme mix, 1 µl of $C_0T$-1 DNA solution (1 µg/µl) and nuclease-free water up to 50 µl was created. This mix was gently vortexed, centrifuged, then incubated at 15° C. for 60 minutes. The reaction was immediately quenched by mixing in 5 µl of 5× stop buffer, then incubated at 65° C. for 5 minutes to denature nick translation enzymes. Nick translation mix was purified using the Qiaquick Nucleotide Removal Kit (Qiagen, #28304). Briefly, 19 ml of 100% isopropanol and 24 ml of 100% ethanol were added to fresh bottles of PNI and PE buffer respectively and mixed. 550 µl (10 volumes) of buffer PNI was added to each nick translation reaction and mixed, then placed into a spin column with a collection tube. The column was centrifuged for 1 minute at 6000 rpm, then the flow-through discarded. 750 µl of buffer PE was added to the column, which was again centrifuged for 1 minute at 6000 rpm and the flow-through discarded. The column was centrifuged for 1 minute at 13,000 rpm to dry the column, then the column transferred to a 1.5 ml collection tube. 50 µl of nuclease-free water was applied to the center of the column and incubated for 1 minute, then eluted by centrifuging for 1 minute at 13,000 rpm. Final yield was determined by UV-Vis absorbance on a Dropsense 96 system (Perkin Elmer).

C. Example 3. Synthesis of RNA Blockers

RNA blockers were synthesized using the HiScribe T7 High Yield RNA Synthesis kit (NEB, #E2040S). Template oligos for i5 and i7 blockers were obtained from IDT (5'-X CCCTATAGTGAGTCGTATTAGTACTCTAGCCTTAA-GATC-3' (SEQ ID NO: 26), 'X' denotes the reverse complement of the blocker sequence to be synthesized) and resuspended to 5 µM. For each blocker template, a transcription mix consisting of 28 µl of nuclease-free water, 3 µl of 10× transcription buffer, 4 µl of NTP mix, 3 µl of T7 RNA polymerase mix, 1 µl of SUPERase RNase Inhibitor (Thermo Fisher, AM2694), and 1 µl of 5 µM input template oligo was created. Transcription mixes were incubated at 37° C. for 2 hours, then cooled to 4° C. Degradation of the template was then performed using DNase I (NEB, #M03035) by aliquoting 50 µl of nuclease-free water, 10 µl of 10× DNase I buffer, and 2 µl of DNase I enzyme into each reaction and pipette mixing. This mix was then incubated at 37° C. for 15 minutes. Transcription products were purified using the Qiagen miRNeasy kit (Qiagen, #217004). Briefly, 1.5 volumes of 100% ethanol was mixed with each reaction and the mixes transferred to spin columns. The columns were centrifuged for 15 seconds at 10,000×g and the flow-through discarded. 500 µl of RPE buffer was added to the columns and the columns centrifuged for 15 seconds at 10,000×g. The previous step was repeated. The columns were transferred to new tubes then centrifuged for 2 minutes at 10,000×g to dry the tubes. Finally, 30 µl of nuclease-free water was added to the center of each column and the columns centrifuged for 1 minute at 10,000×g to elute the RNA. The previous step was repeated to maximize yield. Final yield was determined by UV-Vis absorbance on a Dropsense 96 system (Perkin Elmer).

D. Example 4. Hybridization of Biotinylated Probe to Multiplex Library

2 µg of biotinylated $C_0T$-1 DNA baits, 200 ng of multiplexed DNA sequencing libraries (up to 24 indexed samples), and 10 µg of RNA blockers were combined with pre-warmed hybridization buffer concentrate to a total volume of 10 µl hybridization mix (6×SSC, 0.1% SDS, 4% dextran sulfate, 4 mM EDTA, 4×Denhardt's solution). After vortexing, the mixture was heat denatured at 95° C. for 5 minutes, then incubated at 65° C. for 18 hours to hybridize.

E. Example 5. Removal of Biotinylated Hybrids

A 100 µl aliquot of Dynabeads MyOne Streptavidin T1 (Invitrogen) was warmed to room temperature then washed three times with 1× bind and wash (B&W) buffer (1 M NaCl, 10 mM Tris-HCl pH 8.0, 1 mM EDTA, 0.01% Tween-20) and resuspended in 40 µl of 1×B&W buffer. These resuspended beads were then warmed to 65° C. and added to the 10 µl hybridization mixture and vortexed. This mixture was placed on a thermomixer for gentle vortexing (~1000 rpm) at 65° C. for 15 minutes to allow binding of the biotinylated complex with streptavidin. The tube was placed on a magnetic separation rack and held until the beads completely separated from the supernatant. The supernatant was then transferred to a separate tube.

F. Example 6. Removal of Blockers from Supernatant and Library Quantification 0.5 µl of RNase A (Thermo Fisher Scientific) was added to the supernatant, pipetted to mix, then incubated at room temperature for 15 minutes. The supernatant was then purified using Kapa Pure Beads as described in Example 2, then quantified using the Kapa Library Quantification Kit for Illumina (Roche, #KK4873).

G. Example 7. Sequencing and Data Analysis

Figure 2:
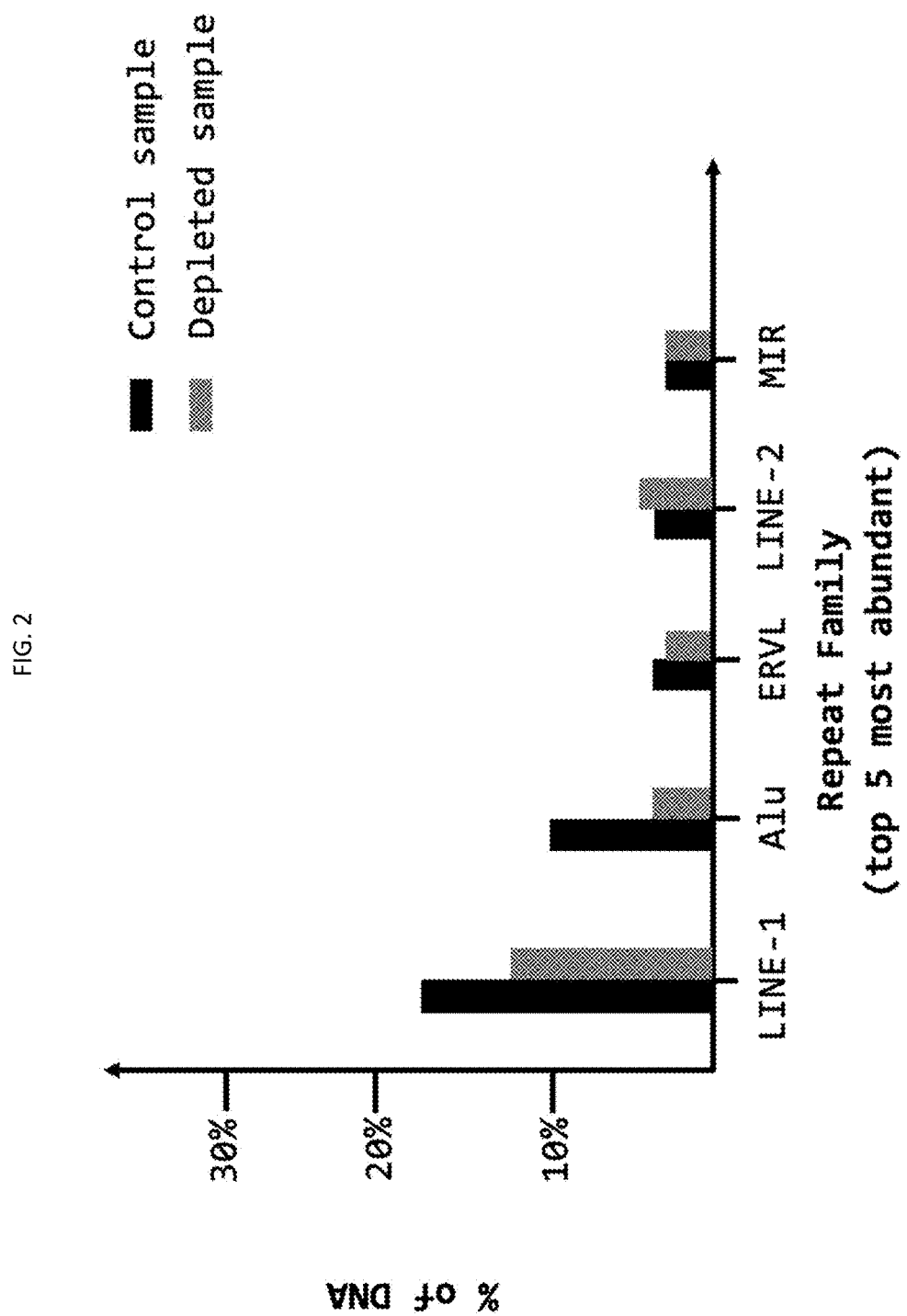
FIG. 2 is provided to illustrate that the capture fraction contains a high proportion of repeat elements (i.e., equal to the proportion present in Cot-1 DNA).

Sequencing was performed with a Nextseq High Output Kit v2.5 (150 cycles) at 4 pM loading concentration on a Nextseq 550. Sequencing data was demultiplexed with bcl2fastq then aligned to hg19 using Bowtie2. To determine the percentage of high-copy repetitive sequences depleted in the human DNA samples, the percentage of aligned reads mapping to annotations in the RepeatMasker 4.1.0 track was calculated using bamtools. FIG. 2 shows that the percentage of high-copy L1 and Alu repeat classes were substantially lower in a depleted sample vs. its non-depleted control.

H. Exemplary Blocker Oligonucleotides (Prophetic)

Examples of blocker oligonucleotides that hybridize to the i7 (Illumina), i5 (Illumina), P1 (Themofisher) and A1 (Themofisher) adaptors are listed in the tables below. The DNA blockers contain deoxyribose uracil (dU, 2-deoxyuridine) that renders to oligonucleotide susceptible to degradation in the presence of Uracil-DNA glycosylase. The oligo(N) sequence (e.g., $[N]_{6-10}$) is the index sequence.

| RNA Blocker oligonucleotide hybridizing to i7 adaptor |
|---|
| CAAGCAGAAGACGGCAUACGAGAUNNNNNNNNNNGUCUCGUGGGCUCGG (SEQ ID NO: 1) |
| CAAGCAGAAGACGGCAUACGAGAUNNNNNNCGGUCUGCCUUGCCAGCCCGCUCAG (SEQ ID NO: 3) |
| CAAGCAGAAGACGGCAUACGAGAUNNNNNNNNNGUCUCGUGGGCUCGGAGAUGUGUAUAAGAGACAG (SEQ ID NO: 5) |
| CAAGCAGAAGACGGCAUACGAGAUNNNNNNNNNGUGACUGGAGUUCAGACGUGUGCUCUUCCGAUC (SEQ ID NO: 7) |
| AAUGAUACGGCGACCACCGAGAUCUACACNNNNNNNNACACUCUUUCCCUACACGACGCUCUUCCGAUCU (SEQ ID NO: 8) |
| CAAGCAGAAGACGGCAUACGAGAUNNNNNNGUGACUGGAGUUCCUUGGCACCCGAGAAUUCCA (SEQ ID NO: 10) |

| RNA Blocker oligonucleotide hybridizing to i5 adaptor |
|---|
| AAUGAUACGGCGACCACCGAGAUCUACACNNNNNNNNNUCGUCGGCAGCGUC (SEQ ID NO: 2) |
| AAUGAUACGGCGACCACCGAGAUCUACACGCCUCCCUCGCGCCAUCAG (SEQ ID NO: 4) |
| AAUGAUACGGCGACCACCGAGAUCUACACNNNNNNNNUCGUCGGCAGCGUCAGAUGUGUAUAAGAGACAG (SEQ ID NO: 6) |
| AAUGAUACGGCGACCACCGAGAUCUACACUCUUUCCCUACACGACGCUCUUCCGAUCU (SEQ ID NO: 9) |
| AAUGAUACGGCGACCACCGAGAUCUACACGUUCAGAGUUCUACAGUCCGA (SEQ ID NO: 11) |

| RNA Blocker oligonucleotide hybridizing to P1 adaptor |
|---|
| CCACUACGCCUCCGCUUUCCUCUCUAUGGGCAGUCGGUGAUAUCACCGACUGCCCAUAGAGAGGAAAGCGGAGGCGUAGUGGUU (SEQ ID NO: 12) |

| RNA Blocker oligonucleotide hybridizing to A1 adaptor |
|---|
| CCAUCUCAUCCCUGCGUGUCUCCGACUCAGNNNNNNNNNGAUAUCGUUACCUUAGCUGAGUCGGAGACACGC (SEQ ID NO: 13) |

| DNA Blocker oligonucleotides containing uracil (dU) and hybridizing to i7 adaptor |
|---|
| d(CAAGCAGAAGACGGCAUACGAGAUNNNNNNNNNNGUCUCGUGGGCUCGG) (SEQ ID NO: 14) |
| d(CAAGCAGAAGACGGCAUACGAGAUNNNNNNCGGUCUGCCUUGCCAGCCCGCUCAG) (SEQ ID NO: 16) |
| d(CAAGCAGAAGACGGCAUACGAGAUNNNNNNNNNGUCUCGUGGGCUCGGAGAUGUGUAUAAGAGACAG) (SEQ ID NO: 18) |
| d(CAAGCAGAAGACGGCAUACGAGAUNNNNNNNNNGUGACUGGAGUUCAGACGUGUGCUCUUCCGAUC) (SEQ ID NO: 20) |
| d(AAUGAUACGGCGACCACCGAGAUCUACACNNNNNNNNACACUCUUUCCCUACACGACGCUCUUCCGAUCU) (SEQ ID NO: 21) |
| d(CAAGCAGAAGACGGCAUACGAGAUNNNNNNGUGACUGGAGUUCCUUGGCACCCGAGAAUUCCA) (SEQ ID NO: 23) |

| DNA Blocker oligonucleotide containing uracil (dU) and hybridizing to i5 adaptor |
|---|
| d(AAUGAUACGGCGACCACCGAGAUCUACACNNNNNNNNNUCGUCGGCAGCGUC) (SEQ ID NO: 15) |
| d(AAUGAUACGGCGACCACCGAGAUCUACACGCCUCCCUCGCGCCAUCAG) (SEQ ID NO: 17) |

```
d(AAUGAUACGGCGACCACCGAGAUCUACACNNNNNNNNNUCGUCGGCAGCGUCAGAUGUGUAUAAGAGACAG)
(SEQ ID NO: 19)

d(AAUGAUACGGCGACCACCGAGAUCUACACUCUUUCCCUACACGACGCUCUUCCGAUCU) (SEQ ID NO: 22)

d(AAUGAUACGGCGACCACCGAGAUCUACACGUUCAGAGUUCUACAGUCCGA) (SEQ ID NO: 24)
```

VIII. Examplary Embodiments

Exemplary embodiments provided in accordance with the presently disclosed subject matter include, but are not limited to, the claims and the following embodiments:

1. A method for preparing a depleted sequencing library comprising:
a) providing a composition comprising a heterogeneous mixture of linear nucleic acids that having a first terminus and a second terminus, wherein the mixture comprises a plurality of target nucleic acids and a plurality of non-target nucleic acids, wherein
   at least some of the plurality of target nucleic acids and at least some of the plurality of non-target nucleic acids comprise an at least partially double-stranded first adaptor region at the first terminus and an at least partially double-stranded second adaptor region at the second terminus and their 5' termini, wherein the first adaptor region comprises a first adaptor sequence and a sequence at least partially complementary to the first adaptor sequence and
   at least some of the plurality of target nucleic acids and at least some of the plurality of non-target nucleic acids comprise the at least partially double-stranded second adaptor region at the first terminus and the at least partially double-stranded second adaptor region at the second terminus, wherein the second adaptor region comprises a second adaptor sequence and a sequence at least partially complementary to the second adaptor sequence;
b) adding removable blocker oligonucleotides to the composition, wherein the removable blocker oligonucleotides comprise:
   (i) first removable blocker oligonucleotides that can anneal to the first adaptor sequence;
   (ii) optionally first complementary removable blocker oligonucleotides that can anneal to the sequence substantially complementary to the first adaptor sequence;
   (iii) second removable blocker oligonucleotides that can anneal to the second adaptor sequence;
   (iv) optionally second complementary removable blocker oligonucleotides that can anneal to the sequence substantially complementary to the second adaptor sequence;
   wherein at least one of the removable blocker oligonucleotides selected from the removable blocker oligonucleotides in (i), (ii), (iii), and (iv) is added in excess over the adaptor sequence to which it hybridizes so that a quantity of said at least one of the removable blocker oligonucleotides is not annealed to an adaptor sequence and is free in solution;
c) removing non-target nucleic acids from the composition by sequence capture to bait oligonucleotides thereby depleting non-target nucleic acids from the composition; and then,
d) treating the composition to reduce a quantity of free blocker oligonucleotides that are not annealed to an adaptor sequence or to a sequence substantially complementary to an adaptor sequence
   whereby the composition comprises a depleted sequencing library.

2. The method of embodiment 1, wherein Step (d) comprises treating the composition to reduce the quantity of the first removable blocker oligonucleotides that are annealed to first adaptor sequences and/or a quantity of the second removable blocker oligonucleotides are annealed to second adaptor sequences.

3. The method of embodiment 2, wherein the blocker oligonucleotides that are annealed and the blocker oligonucleotides that are not annealed are removed at the same time under the same conditions.

4. The method of any one of embodiments 1 to 3, further comprising
e) obtaining the plurality of target nucleic acids from the depleted sequencing library; and
f) sequencing at least a portion of the plurality of target nucleic acids.

5. The method of any one of embodiments 1 to 4, wherein the removable blocker oligonucleotides are RNA oligonucleotides.

6. The method of embodiment 5, wherein the removable blocker oligonucleotides are degraded by an enzyme.

7. The method of embodiment 6, wherein the enzyme is an RNase.

8. The method of embodiment 5, wherein the removable blocker oligonucleotides are degraded by heat.

9. The method of embodiment 5, wherein the removable blocker oligonucleotides are degraded by a combination of heat, addition of divalent ions, optionally Mg2+, and high pH.

10. The method of any one of embodiments 1 to 4, wherein the removable blocker oligonucleotides are DNA oligonucleotides.

11. The method of embodiment 6, wherein the DNA oligonucleotides comprise uracil.

12. The method of embodiment 11, wherein the blocker oligonucleotides can be degraded by an uracil-DNA-glycosylase.

13. The method of any one of embodiments 1 to 12, wherein the removable blocker oligonucleotides are from 40 to 80 nucleotides in length.

14. The method of any one of embodiments 1 to 13, wherein the non-target nucleic acids are high copy nucleic acid sequences, transposable elements, tandem repeats, highly transcribed genes, high-copy contaminating DNAs, and/or CRISPR repeats.

15. The method of any one of embodiments 1 to 14, wherein the composition comprises the nucleic acids isolated from multiple samples.

16. The method of embodiment 15, wherein the nucleic acids from each sample are labeled with a sample-specific barcode sequence.

17. The method of any one of embodiments 1 to 16, wherein the bait oligonucleotides comprise an affinity label that enables subsequent capture of the non-target nucleic acids.

18. The method of embodiment 17, wherein the affinity label is a biotin group.

What is claimed is:

1. A method for preparing a depleted sequencing library comprising:
   a) providing a composition comprising a heterogeneous mixture of linear nucleic acids having a first terminus and a second terminus, wherein the heterogeneous mixture comprises a plurality of target nucleic acids and a plurality of non-target nucleic acids, wherein a first subset of the plurality of target nucleic acids and a second subset of the plurality of non-target nucleic acids comprise an at least partially double-stranded first adaptor region at the first terminus and an at least partially double-stranded second adaptor region at the second terminus, wherein the first adaptor region comprises a first adaptor sequence and a sequence at least partially complementary to the first adaptor sequence, wherein the second adaptor region comprises a second adaptor sequence and a sequence at least partially complementary to the second adaptor sequence, and
      a third subset of the plurality of target nucleic acids and a fourth subset of the plurality of non-target nucleic acids comprise the at least partially double-stranded second adaptor region at the first terminus and the at least partially double-stranded second adaptor region at the second terminus;
   b) adding removable blocker oligonucleotides to the composition, wherein at least a portion of the removable blocker oligonucleotides are RNA oligonucleotides, and wherein the removable blocker oligonucleotides comprise:
      (i) first removable blocker oligonucleotides that can anneal to the first adaptor sequence; and
      (ii) second removable blocker oligonucleotides that can anneal to the second adaptor sequence;
   wherein at least one of the removable blocker oligonucleotides selected from the removable blocker oligonucleotides in (i) and (ii) is added in excess over the adaptor sequence to which it hybridizes so that a quantity of said at least one of the removable blocker oligonucleotides is not annealed to an adaptor sequence and is free in solution;
   c) removing non-target nucleic acids from the composition by sequence capture to bait oligonucleotides thereby depleting non-target nucleic acids from the composition; and
   d) treating the composition by at least an addition of divalent ions to reduce a quantity of the RNA oligonucleotides that are not annealed to an adaptor sequence or to a sequence substantially complementary to an adaptor sequence,
   whereby the composition comprises a depleted sequencing library.

2. The method of claim 1, wherein Step (d) comprises treating the composition to reduce the quantity of the first removable blocker oligonucleotides that are annealed to first adaptor sequences and/or a quantity of the second removable blocker oligonucleotides are annealed to second adaptor sequences.

3. The method of claim 2, wherein the blocker oligonucleotides that are annealed and the blocker oligonucleotides that are not annealed are removed at the same time under the same conditions.

4. The method of claim 1, further comprising
   e) obtaining the plurality of target nucleic acids from the depleted sequencing library; and
   f) sequencing at least a portion of the plurality of target nucleic acids.

5. The method of claim 1, wherein the RNA oligonucleotides are further degraded by an enzyme.

6. The method of claim 5, wherein the enzyme is an RNase.

7. The method of claim 5, wherein the RNA oligonucleotides are further degraded by heat of at least 70° C. for at least one minute.

8. The method of claim 1, wherein the RNA oligonucleotides are degraded by a combination of heat of at least 70° C. for at least one minute, the addition of divalent ions, and a pH greater than 7.

9. The method of claim 1, wherein at least another portion of the removable blocker oligonucleotides are DNA oligonucleotides.

10. The method of claim 9, wherein the DNA oligonucleotides comprise uracil.

11. The method of claim 10, wherein the DNA oligonucleotides can be degraded by an uracil-DNA-glycosylase.

12. The method of claim 1, wherein the removable blocker oligonucleotides are from 40 to 80 nucleotides in length.

13. The method of claim 1, wherein the non-target nucleic acids are high-copy nucleic acid sequences, transposable elements, tandem repeats, highly transcribed genes, high-copy contaminating DNAs, and/or CRISPR repeats.

14. The method of claim 1, wherein the composition comprises linear nucleic acids isolated from multiple samples.

15. The method of claim 14, wherein the nucleic acids from each sample are labeled with a sample-specific barcode sequence.

16. The method of claim 1, wherein the bait oligonucleotides comprise an affinity label that enables subsequent capture of the non-target nucleic acids.

17. The method of claim 16, wherein the affinity label is a biotin group.

* * * * *

SEQUENCE LISTING

<160> NUMBER OF SEQ ID NOS: 26

<210> SEQ ID NO 1
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(34)
<223> OTHER INFORMATION: a, c, u, g, unknown or other

<400> SEQUENCE: 1
caagcagaag acggcauacg agaunnnnnn nnnngucucg ugggcucgg                49

<210> SEQ ID NO 2
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(39)
<223> OTHER INFORMATION: a, c, u, g, unknown or other

<400> SEQUENCE: 2
aaugauacgg cgaccaccga gaucuacacn nnnnnnnnnu cgucggcagc guc            53

<210> SEQ ID NO 3
<211> LENGTH: 55
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(30)
<223> OTHER INFORMATION: a, c, u, g, unknown or other

<400> SEQUENCE: 3
caagcagaag acggcauacg agaunnnnnn cggucugccu ugccagcccg cucag          55

<210> SEQ ID NO 4
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aaugauacgg cgaccaccga gaucuacacg ccucccucgc gccaucag                  48

<210> SEQ ID NO 5
<211> LENGTH: 66
<212> TYPE: RNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (25)..(32)
<223> OTHER INFORMATION: a, c, u, g, unknown or other

<400> SEQUENCE: 5
caagcagaag acggcauacg agaunnnnnn nngucucgug ggcucggaga uguguauaag    60
agacag                                                              66

<210> SEQ ID NO 6
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(37)
<223> OTHER INFORMATION: a, c, u, g, unknown or other

<400> SEQUENCE: 6
aaugauacgg cgaccaccga gaucuacacn nnnnnnnucg ucggcagcgu cagaugugua    60
uaagagacag                                                          70

<210> SEQ ID NO 7
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(32)
<223> OTHER INFORMATION: a, c, u, g, unknown or other

<400> SEQUENCE: 7
caagcagaag acggcauacg agaunnnnnn nngugacugg aguucagacg ugugcucuuc    60
cgauc                                                               65

<210> SEQ ID NO 8
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(37)
<223> OTHER INFORMATION: a, c, u, g, unknown or other

<400> SEQUENCE: 8
aaugauacgg cgaccaccga gaucuacacn nnnnnnaca cucuuucccu acacgacgcu    60
cuuccgaucu                                                          70

<210> SEQ ID NO 9
<211> LENGTH: 58
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
```

```
aaugauacgg cgaccaccga gaucuacacu cuuucccuac acgacgcucu uccgaucu        58

<210> SEQ ID NO 10
<211> LENGTH: 63
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(30)
<223> OTHER INFORMATION: a, c, u, g, unknown or other

<400> SEQUENCE: 10
caagcagaag acggcauacg agaunnnnnn gugacuggag uuccuuggca cccgagaauu      60
cca                                                                   63

<210> SEQ ID NO 11
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
aaugauacgg cgaccaccga gaucuacacg uucagaguuc uacaguccga                 50

<210> SEQ ID NO 12
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ccacuacgcc uccgcuuucc ucucuauggg cagucgguga uauccaccgac ugcccauaga    60 gaggaaagcg gaggcguagu gguu                                            84

<210> SEQ ID NO 13
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(40)
<223> OTHER INFORMATION: a, c, u, g, unknown or other

<400> SEQUENCE: 13
ccaucucauc ccugcguguc uccgacucag nnnnnnnnnn gauaucguua ccuuagcuga     60
gucggagaca cgc                                                        73

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
          Synthetic oligonucleotide
<220> FEATURE:
<221> NAME/KEY: modified_base
<222> LOCATION: (25)..(34)
<223> OTHER INFORMATION: a, c, t, g, unknown or other

<400> SEQUENCE: 14
caagcagaag acggcauacg agaunnnnnn nnnngucucg ugggcucgg              49

<210> SEQ ID NO 15
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(39)
<223> OTHER INFORMATION: a, c, t, g, unknown or other

<400> SEQUENCE: 15
aaugauacgg cgaccaccga gaucuacacn nnnnnnnnnu cgucggcagc guc          53

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(30)
<223> OTHER INFORMATION: a, c, t, g, unknown or other

<400> SEQUENCE: 16
caagcagaag acggcauacg agaunnnnnn cggucugccu ugccagcccg cucag        55

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
aaugauacgg cgaccaccga gaucuacacg ccucccucgc gccaucag                48

<210> SEQ ID NO 18
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (25)..(32)
<223> OTHER INFORMATION: a, c, t, g, unknown or other

<400> SEQUENCE: 18
caagcagaag acggcauacg agaunnnnnn nngucucgug ggcucggaga uguguauaag    60
agacag                                                              66

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(37)
<223> OTHER INFORMATION: a, c, t, g, unknown or other

<400> SEQUENCE: 19
aaugauacgg cgaccaccga gaucuacacn nnnnnnnucg ucggcagcgu cagaugugua    60
uaagagacag                                                          70

<210> SEQ ID NO 20
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(32)
<223> OTHER INFORMATION: a, c, t, g, unknown or other

<400> SEQUENCE: 20
caagcagaag acggcauacg agaunnnnnn nngugacugg aguucagacg ugcgcucuuc    60
cgauc                                                               65

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(37)
<223> OTHER INFORMATION: a, c, t, g, unknown or other

<400> SEQUENCE: 21
aaugauacgg cgaccaccga gaucuacacn nnnnnnaca cucuuucccu acacgacgcu    60
cuuccgaucu                                                          70

<210> SEQ ID NO 22
<211> LENGTH: 58
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
aaugauacgg cgaccaccga gaucuacacu cuuucccuac acgacgcucu uccgaucu         58

<210> SEQ ID NO 23
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(30)
<223> OTHER INFORMATION: a, c, t, g, unknown or other

<400> SEQUENCE: 23
caagcagaag acggcauacg agaunnnnnn gugacuggag uuccuuggca cccgagaauu         60
cca                                                                      63

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
aaugauacgg cgaccaccga gaucuacacg uucagaguuc uacaguccga                   50

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments
```

```
<400> SEQUENCE: 26
ccctatagtg agtcgtatta gtactctagc cttaagatc                                      39
```